United States Patent [19]

Perren

[11] 4,197,459

[45] Apr. 8, 1980

[54] ELECTRO-OPTICAL DEVICE FOR THE DETECTION OF THE PRESENCE OF LIQUID

[76] Inventor: Benno Perren, Austrasse 33, 5430 Wettingen, Switzerland

[21] Appl. No.: 929,851

[22] Filed: Jul. 31, 1978

[51] Int. Cl.² .................................................. G01J 1/00
[52] U.S. Cl. ..................................... 250/341; 250/353
[58] Field of Search ............... 250/338, 341, 343, 344, 250/353, 357

[56] References Cited

U.S. PATENT DOCUMENTS

| | | | |
|---|---|---|---|
| 3,906,232 | 9/1975 | Meihofer | 250/338 |
| 4,020,345 | 4/1977 | Meyer | 250/343 |

Primary Examiner—Alfred E. Smith
Assistant Examiner—Janice A. Howell
Attorney, Agent, or Firm—Werner W. Kleeman

[57] ABSTRACT

An electro-optical device for the detection of the presence of a liquid, comprising at least one monochromatic infrared transmitter arranged at the region of a hollow body probe composed of a synthetic high molecular substance and totally reflecting the infrared radiation. There are also provided at least one infrared receiver and a circuit for signal processing. At least at the region of at least a boundary surface which totally reflects the infrared radiation the hollow body probe consists of a halogen-containing polymerizate.

6 Claims, 4 Drawing Figures

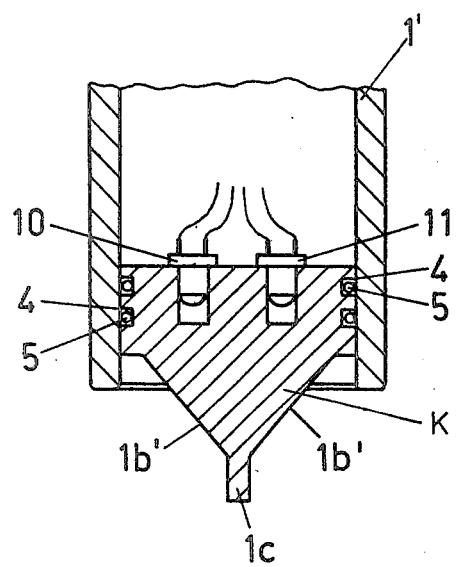
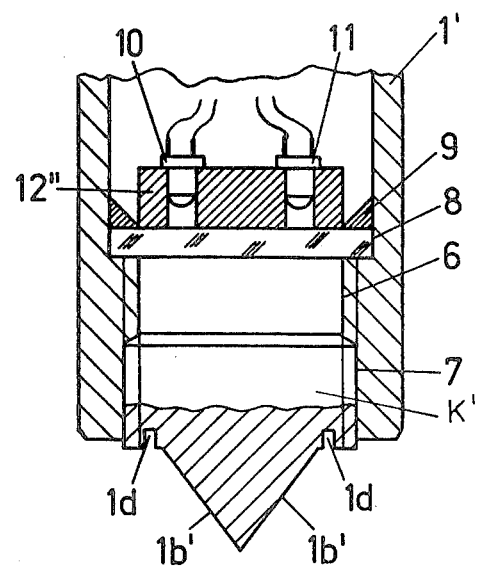
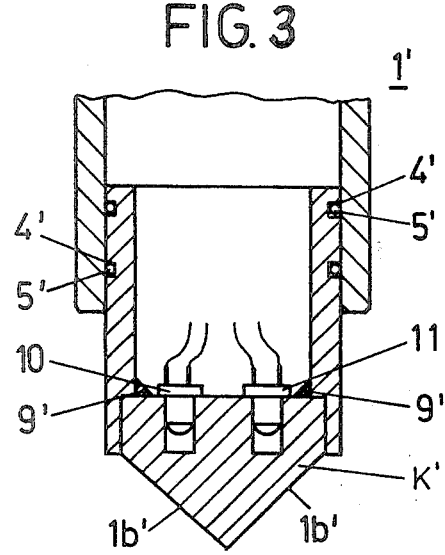
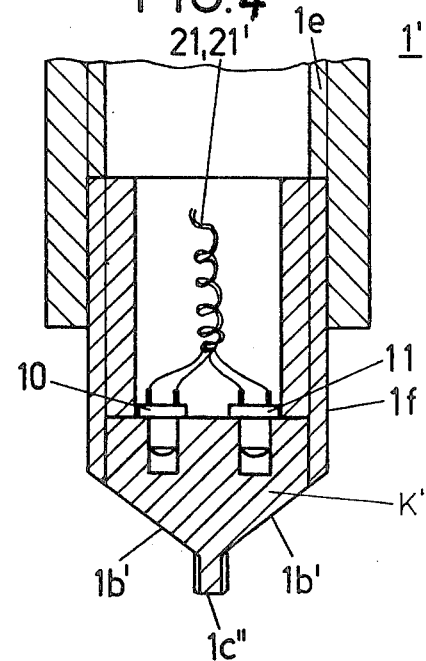

ELECTRO-OPTICAL DEVICE FOR THE DETECTION OF THE PRESENCE OF LIQUID

BACKGROUND OF THE INVENTION

The present invention concerns a new and improved construction of electro-optical device for the detection of the presence of a liquid, which is of the type comprising at least one monochromatic infrared transmitter which is arranged at the region of a hollow body probe composed of a synthetic high molecular substance or material, meaning a polymerized substance or material, and totally reflecting the infrared radiation, as well as there being provided at least one infrared receiver and a circuit for signal processing.

Such equipment is designated in the art as liquid sensors or feelers. In Swiss Pat. No. 512,060 there is taught to the art a compact structural unit which has a high response sensitivity and is extensively non-sensitive to mechanical loads and does not require any subsequent adjustments.

The light-conducting body, used with the prior art equipment, for the detection of the presence of liquid must have high optical transparency, and therefore, in practice is fabricated from acrylic glass.

Owing to the limited resistance of acrylic glass as well as similar light-conducting products with respect to liquids which can be considered to be aggressive, the use of such type liquid sensors is limited as is also their longevity or service life.

All of the heretofore known liquid sensors or feelers additionally require a relatively high transmission energy of the light-emitting diode, in order to insure for a reproducible response behavior. It is known that for this reason the employment of such type devices, especially the use thereof in conjunction with highly explosive media, is prohibited for safety reasons in a number of countries.

SUMMARY OF THE INVENTION

Therefore, it is a primary object of the present invention to provide a new and improved construction of an electro-optical device for the detection of the presence of liquids which is not associated with the aforementioned drawbacks and limitations of the prior art proposals.

Another and more specific object of the present invention aims at providing a compact construction of an electro-optical device for the detection of also even chemically aggressive liquids, which, additionally, is easy to clean and relatively non-sensitive to contamination and the formation of crust or scale due to crystallization of the liquid and so forth.

A further object of the invention is to provide an electro-optical device for the detection of the presence of liquids which, owing to the low requisite transmitting energy, also can be employed in the environment of highly explosive liquids.

Now in order to implement these and still further objects of the invention, which will become more readily apparent as the description proceeds, the hollow body probe, at least at the region of at least one boundary surface which totally reflects the infrared radiation, consists of a halogen-containing polymerizate.

The teachings of the present invention render possible, with the use of inexpensive means, the construction of electro-optical devices for the detection of liquids and which can be accommodated to a great degree to the momentarily encountered installation conditions.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a fragmentary sectional view of a body arranged to be axially displaceable in a hollow body probe and formed of a halogen-containing polymerizate and having totally reflecting boundary surfaces;

FIG. 2 illustrates in fragmentary sectional view a further construction containing a body of a hollow body probe which can be axially adjusted by means of fine threads;

FIG. 3 is a fragmentary sectional view of a further construction of a hollow body probe which can be adjusted in a telescope-like fashion; and FIG. 4 is a fragmentary sectional view of a hollow body probe which can be adjusted by a threading action.

DETAILED DESCRIPTION OF THE INVENTION

Describing now the drawings, in FIG. 1 there is illustrated a hollow body probe 1' essentially composed of a tube in which there is axially displaceably arranged a substantially rotationally symmetrical body or body member K having totally reflecting boundary surfaces or boundary surface means 1b' and fabricated, for instance, from perfluoroalkoxy (PFA).

In the outer or jacket surface of the body K there are formed two annular or ring-shaped grooves 4, in each of which there is mounted a respective sealing ring 5 formed of, for instance, fluoroethylenepropylene (FEP; "TEFLON").

Basically, the mode of operation of such type electro-optical device is known. The infrared transmitter 10 which contains a LED-diode (for instance of the commercially available type 1A 48 which can be obtained from ASEA) irradiates a monochromatic infrared radiation of about 940 nm having a spectral bandwidth of 60 nm, which in part is totally reflected at the totally reflecting boundary surface 1b' and deflected to the oppositely situated boundary surface. Since at this boundary surface there again occurs a certain total reflection, an infrared signal is received by an infrared receiver 11 having a silicon PIN-diode (for instance of the commercially available type S 138 P from the well known German firm Telefunken AG).

If the boundary surfaces 1b' immerse in a liquid, then the previously described optical transmission path is interrupted, since the infrared radiation now enters the liquid. At this point the signal processing begins.

Hence, by means of an electro-optical device of the type shown in FIG. 1, it is possible to adjust the height of a liquid level which is to be monitored by displacing the body K through a range of up to about 2 cm.

The tapered portion or taper 1c provided at the body or body member K insures for a rapid outflow of any liquid film which may possible adhere at the boundary surfaces 1b'.

The once adjusted working height of the electro-optical device and, thus, the liquid level to be monitored, also can be determined with the hereinafter described devices with known means, for instance by means of an adjustment screw or equivalent structure which is effective at the body K.

The embodiment of electro-optical device shown in FIG. 2 will be seen to possess an internally stepped hollow body 1' having fine internal threads 6.

At the region of the fine internal threads 6 a body or body member K' fabricated of fluoroethylenepropylene (FEP) can be adjusted by means of fine external threads 7 by screwing such to a greater or lesser extent into hollow body probe 1'.

The body K' can be rotated by means of a tubular wrench or other suitable tool equipped at its end face with dogs or protuberences or the like and which dogs engage into the bore 1d of the body or body member K'.

With this exemplary embodiment the boundary surfaces 1b' merge into a tip. When working with liquids with low viscosity there is thus beneficially insured for an off-flow or dripping-off of the liquid at the boundary surfaces 1b' which have been immersed in the liquid.

It is known that a screw connection composed of fine threads is not absolutely fluidtight or gastight. It is for this reason that at the stepped part of the hollow body probe 1' there is adhesively bonded by means of a seal 9 a glass body 8.

In the embodiment under discussion this glass body 8 is an infrared filter, but also could be however, for instance, in the case of a not particularly aggressive environment, formed of acrylic glass which is bonded in a hollow body probe 1' formed of polyvinylchloride (PVC).

The infrared transmitter 10 and the infrared receiver 11 are mounted in a centering sleeve 12" and operated in conventional fashion. In this regard further details have been disclosed in my U.S. application Ser. No. 929,850, filed July 31, 1978, entitled "Electro-Optical Apparatus For The Detection Of The Presence Of Liquid", to which reference may be readily had and the disclosure of which is incorporated herein by reference.

Instead of having an electro-optical device formed of individual elements the hollow body probe 1', the glass body 8 as well as the centering sleeve 12' could be fabricated from a transparent, one-piece plastic, for instance from an injection molded part.

The variant embodiment of electro-optical device shown in FIG. 3 will be seen to comprise a body or body member K' formed of polyvinyl fluoride (PVF) which is pressed into a hollow body probe 1' formed of two parts. A seal or sealing member 9' formed of plastic rubber affords an additional protection against the penetration of gases at the end face of the arrangement.

The adjustment of the working height of the electro-optical device occurs in the manner already described in conjunction with FIG. 1.

The ring-shaped grooves 4' are equipped with resistant sealing rings or seals 5', for instance synthetic rubber O-rings, which, owing to their rolling movement, allow for a precise adjustment of the working height throughout wide limits.

Now in FIG. 4 there is shown the principle which is analogous to FIG. 3, however with threadable hollow body probe 1', wherein signal lines or conductors 21 and 21' are intertwined and lead to the infrared transmitter 10 and infrared receiver 11.

A relatively long connection means composed of the precision threads 1e and 1f serves as a labyrinth seal for possibly arising vapors, and additionally, is provided with a chemically neutral lubricant film.

For the easy adjustment of the electro-optical device there is beneficially employed a hexagonal-shaped tapered portion or taper 1c''', which additionally functions as a drip nose.

Through the use of selected infrared transmitters in conjunction with the novel hollow body probes it is possible to reduce the transmitting energy needed for operating the electro-optical device to less than 30 mW.

Especially when using halogen-containing polymerizates it is important that there be present as axially symmetrical radiation distribution as possible for the infrared transmitter. As an optimum in this regard it has been found to be beneficial to have a spatial distribution of the radiation intensity in the plane of half power with a half-angle aperture of less than 4°.

The thus selected infrared transmitters 10 are operated with radiation outputs of 15 to 30 mW/sterad and thus fulfill also the safety requirements when used in conjunction with highly explosive liquids.

Of course, the invention herein disclosed is not limited to adjustable devices. The exemplary embodiments, as well equally the materials used for designing the same, illustrate the extreme adaptability of the invention and therefore must be appropriately varied to accommodate the momentarily encountered conditions.

For instance, it is recommended, when using electro-optical devices which must monitor the level of liquids having a relatively high liquefying point, to employ at least one heating element which is arranged at the region of the totally reflecting boundary surface of the hollow body probe, as the same has been disclosed more fully in my aforementioned U.S. application, Ser. No. 929,850.

Particularly suitable for this purpose are PTC-resistors, which either are powered by the signal lines or signal cable already present at the electro-optical device, or can be externally powered in order to reduce the disturbances at the optical transmission path.

Finally, it is mentioned that at least one body, such as the body K or K' of the hollow body probe contains a halogen-containing polymerizate selected from the group consisting essentially of: fluoroethylenepropylene, perfluoroalkoxy, polychlorotrifluoroethylene, ethylene-chlorotrifluoroethylene, ethylenetetrafluoroethylene, polyvinyl fluoride and polyvinylidene fluoride, and polytetrafluoroethylene.

While there are shown and described present preferred embodiments of the invention, it is to be distinctly understood that the invention is not limited thereto, but may be otherwise variously embodied and practiced within the scope of the following claims.

ACCORDINGLY,

What I claim is:

1. An electro-optical device for the detection of the presence of a liquid, comprising:

a hollow body probe composed of a synthetic, polymerized substance and totally reflective for infrared radiation;

at least one monochromatic infrared transmitter arranged at the region of the hollow body probe;

at least one infrared receiver;

said hollow body probe having at least one boundary surface which totally reflects the infrared radiation; and said hollow body probe containing a halogen-containing polymerizate at least at the region of the boundary surface which totally reflects the infrared radiation.

2. The electro-optical device as defined in claim 1, wherein:

said hollow body probe contains a body formed of a halogen-containing polymerizate selected from the group consisting essentially of: fluoroethylenepropylene, perfluoroalkoxy, polychlorotrifluoroethylene, ethylenechlorotrifluoroethylene, ethylene tetrafluoroethylene, polyvinyl fluoride, polyvinylidene fluoride and polytetrafluoroethylene.

3. The electro-optical device as defined in claim 2, further including:

means for axially displacing said body.

4. The electro-optical device as defined in claim 2, wherein:

said hollow body probe contains at least two parts which are telescopically displaceable within one another.

5. The electro-optical device as defined in claim 1, further including:

at least one heating element arranged at the region of the totally reflecting boundary surface of the hollow body probe.

6. The electro-optical device as defined in claim 1, wherein:

said infrared transmitter has an optical axis;

said infrared transmitter having a maximum radiation intensity of less than about 200 mW/sterad;

the main maximum of the spatial radiation distribution at least being approximately axially symmetrical and aligned essentially in the direction of the optical axis of the infrared transmitter; and the spatial distribution of the radiation intensity in the plane of half power having a half-angle aperture of less than 4°.

* * * * *